United States Patent [19]
Granger et al.

[11] Patent Number: 5,693,330
[45] Date of Patent: *Dec. 2, 1997

[54] SKIN CARE COMPOSITIONS CONTAINING MELINAMIDE AND A RETINOID

[75] Inventors: Stewart Paton Granger, Paramus; Anthony Vincent Rawlings, Warrington; Ian Richard Scott, Allendale, all of N.J.

[73] Assignee: Elizabeth Arden Co., Division of Conopco, Inc., New York, N.Y.

[ * ] Notice: The term of this patent shall not extend beyond the expiration date of Pat. No. 5,599,548.

[21] Appl. No.: 636,811

[22] Filed: Apr. 25, 1996

[51] Int. Cl.$^6$ .................................................. A61K 7/48
[52] U.S. Cl. .................. 424/401; 424/59; 514/844; 514/845; 514/846; 514/847; 514/938
[58] Field of Search .................. 424/401, 59; 514/844, 514/845, 846, 847, 938

[56] References Cited

U.S. PATENT DOCUMENTS

| | | | |
|---|---|---|---|
| 3,883,661 | 5/1975 | Young | 424/320 |
| 4,363,815 | 12/1982 | Yu et al. | 424/274 |
| 4,380,549 | 4/1983 | Van Scott et al. | 424/317 |
| 5,057,501 | 10/1991 | Thornfeldt | 514/53 |
| 5,216,148 | 6/1993 | Klaus et al. | 540/517 |
| 5,308,551 | 5/1994 | Beauquey et al. | 252/548 |

FOREIGN PATENT DOCUMENTS

| | | |
|---|---|---|
| 0 388 275 | 9/1990 | European Pat. Off. . |
| 0 582 458 | 2/1994 | European Pat. Off. . |
| 1126289 | 9/1968 | United Kingdom . |
| 93/19743 | 10/1993 | WIPO . |
| 93/25177 | 12/1993 | WIPO . |
| 94/03156 | 2/1994 | WIPO . |

OTHER PUBLICATIONS

Vahlquist, A. et al., "Isotretinoin Treatment of Severe Acne Affects the Endogenous Concentration of Vitamin A in Sebaceous Glands", *J. Invest Dermatol.*, vol. 94, (1990), pp. 496–498.

Ellis, C. N. et al., "Treatment of Actinically Aged Skin with Topical Tretinoin", *Pharmacology of Retinols in Skin*, vol. 3, (1989), pp. 249–252.

Lowe, N. J. et al., "Systemic Reinoids in Psoriasis: Comparative Efficacy and Toxicity", *Pharmacology of Retinols in Skin*, vol. 3, (1989), pp. 240–248.

Derwent Abstract of WO 94/03156.
Derwent Abstract of EP 0 388 275.
Derwent Abstract of EP 0 559 304.

*Primary Examiner*—Jyothsan Venkat
*Attorney, Agent, or Firm*—Rimma Mitelman

[57] ABSTRACT

Melinamide in combination with either retinol or retinyl ester resulted in a synergistic enhancement in keratinocyte proliferation. The effects of the retinol or retinyl esters in combination with fatty acid amides were analogous to treatment with retinoic acid.

5 Claims, No Drawings

SKIN CARE COMPOSITIONS CONTAINING MELINAMIDE AND A RETINOID

FIELD OF THE INVENTION

The invention relates to skin care compositions containing melinamide and a retinoid, preferably retinol or retinyl ester.

BACKGROUND OF THE INVENTION

Retinol (vitamin A) is an endogenous compound which occurs naturally in the human body and is essential for normal epithelial cell differentiation. Natural and synthetic vitamin A derivatives have been used extensively in the treatment of a variety of skin disorders and have been used as skin repair or renewal agents. Retinoic acid has been employed to treat a variety of skin conditions, e.g., acne, wrinkles, psoriasis, age spots and discoloration. See e.g., Vahlquist, A. et al., *J. Invest. Dermatol.*, Vol. 94, Holland D. B. and Cunliffe, W. J. (1990), pp. 496–498; Ellis, C. N. et al., "Pharmacology of Retinols in Skin", Vasel, Karger, Vol. 3, (1989), pp. 249–252; Lowe, N. J. et al., "Pharmacology of Retinols in Skin", Vol. 3, (1989), pp. 240–248; PCT Patent Application No. WO 93/19743. Retinol and retinyl esters, such as retinyl acetate and retinyl palmitate, are easier to formulate/stabilize than retinoic acid. Unfortunately, retinol and retinyl esters are less effective than retinoic acid at providing skin benefits. The present invention is based, in part, on the discovery that a combination of retinol or retinyl esters with melinamide results in a synergistic improvement in keratinocyte proliferation. The effects of melinamide combined with retinol or a retinyl ester were analogous to the effects of retinoic acid. Thus, a mixture of melinamide with retinol or retinyl esters mimics retinoic acid yet is easier to use than retinoic acid.

Thornfeldt (U.S. Pat. No. 5,057,501) discloses a method for treatment of papulosquamous and eczematous diseases with a composition containing a sesquiterpene compound and from about 0.025% to about 35% of a monocarboxylic fatty acid, ester, or amide. The compositions may also include a retinoid; Thornfeldt teaches that certain retinoids, namely isotretinoin, tretinoin, etretin (all of which are stereoforms of retinoic acid) and etretinate (an ester of trimethoxyphenyl retinoic acid) have proven efficacy against papulosquamous diseases. PCT Application WO/9325177 (Procter and Gamble) discloses compositions for topical application to skin which contain a specific type of acyclic carboxamide coolant and may include retinoids such as retinoic acid and its derivatives (e.g., cis and trans). PCT application WO/9403156 (Rhone Poulenc) discloses a topical composition containing linoleic acid or a derivative as an active ingredient for treatment and prophylaxis of impure skin (e.g., skin affected by pimples, pustules, or comedones); the composition may also contain 0.025–0.1 wt. % of tretinoin. European Patent Application No. 0 388 275 (Pierre Fabre Cosmetique) discloses compositions for treating seborrhea containing alkyl carboxamide and a zinc salt which may be zinc retinoate.

Klaus et al., (U.S. Pat. No. 5,216,148) disclose the use of specific complex carboxamides for treating and preventing neoplasms, dermatoses, and aging of skin. Van Scoff et al. (U.S. Pat. No. 4,380,549) and Yu et al., (U.S. Pat. No. 4,363,815) disclose treatment of acne, dry, flaky, scaly skin with a hydroxyacid or the amide thereof. EP 0 582 458 discloses use of N,N-(1,4 C alkyl) lauramide. EP 0 559 304 disclose the use of an amide containing a hydrocarbyl chain of at least 25 carbon atoms as a skin smoothening agent. Beauquey et al. (U.S. Pat. No. 5,308,551) discloses a skin washing and conditioning composition containing, among other ingredients, a 1–4 C alkanolamide of a 8–16 C fatty acid. Great Britain Patent Specification No. 1,126,289 (Hoffman-La Roche) discloses a stock vitamin preparation containing vitamin A alcohol or a vitamin A ester, an emulsifier and a solvent which is selected from an alcohol or a dialkyl amide of a monocarboxylic acid (e.g., N,N-diethylacetamide, N,N-dimethyl acetamide or N,N-dimethyl formamide). The vitamin preparation has a very high vitamin content, i.e., the minimum concentration is 250,000 I.U. vitamin A/ml. Further, the amides disclosed in the '289 application do not include or mention melinamide.

The art cited above does not disclose skin conditioning compositions based on synergistic combinations of melinamide with retinol or a retinyl ester. None of the art cited above addresses the need for an effective alternative to retinoic acid.

Accordingly, it is an object of the present invention to provide a skin conditioning composition containing a combination of retinol or a retinyl ester with melinamide.

It is another object of the invention to provide a method of conditioning skin with a composition containing as an active system a mixture of melinamide with retinol or a retinyl ester.

It is yet another object of the invention to provide a substitute for retinoic acid in cosmetic compositions.

These and other objects of the invention will become more apparent from the detailed description and examples that follow.

SUMMARY OF THE INVENTION

The above objects are attained by the present invention which includes, in part, a skin conditioning composition containing:

(a) from about 0.001% to about 10% of a retinoid selected from the group consisting of retinol, a retinyl ester, and retinoic acid;

(b) from about 0.0001% to about 50% of melinamide; and (c) a cosmetically acceptable vehicle.

The term "conditioning" as used herein means prevention and treatment of dry skin, photodamaged skin, appearance of wrinkles, age spots, aged skin, acne, skin lightening psoriasis, atopic dermatosis, increasing stratum corneum flexibility, and generally increasing the quality of skin. The composition may be used to improve skin desquamation and cellular proliferation.

The presence of melinamide in the inventive product substantially improves the performance of retinol or a retinyl ester, i.e., melinamide substantially increases the ability of retinol or a retinyl ester to affect cellular proliferation. Melinamide has no or little effect on improving skin benefit when used alone; a substantial increase in skin benefit is only realized when melinamide is combined with retinol or a retinyl ester. In short, the present invention is based, at least in part, on the discovery of synergistic interaction between retinol or a retinyl ester and melinamide.

In a preferred embodiment of the invention, a retinoid is selected from the group consisting of retinol or a retinyl ester. According to the present invention, by virtue of including an effective amount of melinamide into compositions containing retinol or a retinyl ester, the performance of the compositions is substantially improved. Alternatively, lower levels of retinol or a retinyl ester may be included in the composition containing melinamide to equal the performance of a similar formulation without the amide.

DESCRIPTION OF THE PREFERRED EMBODIMENT

The inventive compositions contain, as a first essential ingredient, a compound selected from the group consisting of retinol, a retinyl ester, or retinoic acid.

The term "retinol" includes the following isomers of retinol: all-trans-retinol, 13-cis-retinol, 11-cis-retinol, 9-cis-retinol, 3,4-didehydro-retinol. Preferred isomers are all-trans-retinol, 13-cis-retinol, 3,4-didehydro-retinol, 9-cis-retinol. Most preferred is all-trans-retinol, due to its wide commercial availability.

Retinyl ester is an ester of retinol. The term "retinol" has been defined above. Retinyl esters suitable for use in the present invention are $C_1$–$C_{30}$ esters of retinol, preferably $C_2$–$C_{20}$ esters, and most preferably $C_2$, $C_3$, and $C_{16}$ esters because they are more commonly available. Examples of retinyl esters include but are not limited to: retinyl palmirate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadeconoate, retinyl stearate, retinyl isostearate, retinyl nonadecanoate, retinyl arachidonate, retinyl behenate, retinyl linoleate, retinyl oleate, retinyl lactate, retinyl glycolate, retinyl hydroxy caprylate, retinyl hydroxy laurate, retinyl tarfarate.

The preferred ester for use in the present invention is selected from retinyl palmitate, retinyl acetate and retinyl propionate, because these are the most commercially available and therefore the cheapest.

The term "retinoic acid" includes the following isomers of retinoic acid, all-trans-retinoic acid, 9-cis-retinoic acid, 13-cis-retinoic acid, all-trans-3,4-didehydro-retinoic acid, 13-cis-3,4-didehydroretinoic acid, 9-cis-3,4-didehydroretinoic acid, 9,13-di-cis-3,4-didehydroretinoic acid, 5,6-epoxyretinoic acid, 5,8-epoxyretinoic acid, 4-oxoretinoic acid, 4-oxo-13-cis-retinoic acid.

The retinoid is employed in the inventive composition in an amount of from about 0.001% to about 10%, preferably in an amount of from about 0.01% to about 1%, most preferably in an amount of from about 0.01% to about 0.5%.

The second essential ingredient of the inventive compositions is melinamide. The structure of melinamide is as follows:

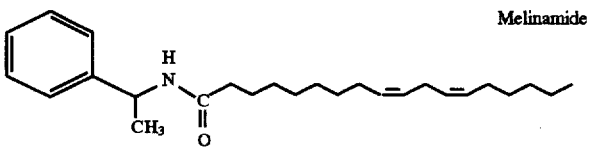

Melinamide

Melinamide is included in the inventive compositions in an amount ranging from about 0.0001% to about 50%, preferably from about 0.01% to about 10%, most preferably from about 0.1% to about 5%.

Optional Skin Benefit Materials and Cosmetic Adjuncts

An oil or oily material may be present, together with an emulsifier to provide either a water-in-oil emulsion or an oil-in-water emulsion, depending largely on the average hydrophilic-lipophilic balance (HLB) of the emulsifier employed.

Various types of active ingredients may be present in cosmetic compositions of the present invention. Various types of active ingredients may be present in cosmetic compositions of the present invention. Actives are defined as skin or hair benefit agents other than emollients and other than ingredients that merely improve the physical characteristics of the composition. Although not limited to this category, general examples include sunscreens, tanning agents.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Another preferred optional ingredient is selected from essential fatty acids (EFAs), i.e., those fatty acids which are essential for the plasma membrane formation of all cells, in keratinocytes EFA deficiency makes cells hyperproliferative. Supplementation of EFA corrects this. EFAs also enhance lipid biosynthesis of epidermis and provide lipids for the barrier formation of the epidermis. The essential fatty acids are preferably chosen from linoleic acid, γ-linolenic acid, homo-γ-linolenic acid, columbinic acid, eicosa-(n-6,9, 13)-trienoic acid, arachidonic acid, γ-linolenic acid, timnodonic acid, hexaenoic acid and mixtures thereof.

Yet another preferred optional ingredient is selected from azoles, e.g., climbazole, bifonazole, clotrimazole, ketoconazole, miconazole, econazole, itraconazole, fluconazole, terconazole, butoconazole, sulconazole, lionazole and mixtures thereof.

Emollients are often incorporated into cosmetic compositions of the present invention. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers, perfumes and preservatives (e.g., imidazolidinyl urea, dimethyl imidazolidinone and diazolidinyl urea). Amounts of these materials may range anywhere from 0.001% up to 20% by weight of the composition.

Use of the Composition

The composition according to the invention is intended primarily as a product for topical application to human skin, especially as an agent for conditioning and smoothening the skin, and preventing or reducing the appearance of wrinkled or aged skin.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

Product Form and Packaging

The topical skin treatment composition of the invention can be formulated as a lotion having a viscosity of from 4,000 to 10,000 mPas, a fluid cream having a viscosity of from 10,000 to 20,000 mPas or a cream or a gel having a viscosity of from 20,000 to 100,000 mPas or above. The composition can be packaged in a suitable container to suit its viscosity and intended use by the consumer. For example, a lotion or fluid cream can be packaged in a bottle or a roll-ball applicator, or a capsule, or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

The following specific examples further illustrate the invention, but the invention is not limited thereto.

MATERIALS AND METHODS

Cell Culture:

Human keratinocytes, isolated from neonatal foreskin by trypsin treatment were grown in Dulbecco Modification Eagle (DME) Hams F12 (1:1) medium/10% fetal calf serum in the presence of irradiated 3T3 mouse fibroblasts for establishing dividing keratinocyte colonies. Cells were grown under the above condition until their second passage and kept frozen for future use. Frozen second passage keratinocytes were thawed and plated into the above medium and grown for five days before they were switched to a serum-free MCDB 153-based medium keratinocyte growth medium (KGM) from Clonetics Corporation, San Diego, Calif., containing 0.15 mM Ca, or keratinocyte serum-free media (KSFM) from GIBCO containing 0.09 mM Ca). On day 7, when the cells were 80–90% confluent, they were trypsinized and plated in the serum-free medium for the various experiments.

Thymidine Assay $^3$H-Thymidine Incorporation and Keratinocyte Proliferation

The incorporation of $^3$H-thymidine by cultured keratinocytes was used as an assay of keratinocyte proliferation. Thymidine is one of four deoxynucleosides which are the monomeric units of DNA, the universal library of genetic information in the animal kingdom. Prior to cell division of a somatic cell such as a keratinocyte, the complete genome of the cell undergoing cell division is replicated. This involves large scale DNA synthesis by the cell and enables both daughter cells to receive identical copies of the genetic material. When $^3$H-thymidine is included in the culture media of keratinocytes which are synthesizing DNA in preparation for cell division then the labelled nucleoside is incorporated into the newly synthesized DNA. The extent of incorporation of $^3$H-thymidine into a population of cells is proportional to the rate of DNA synthesis by this population of cells and therefore an indication of their cellular proliferation.

Keratinocytes (that were cultured as described above) were plated in 24 well plates at a density of 40,000 cells per well in 1 ml media. After incubation for four days or until the cells were 60–70% confluent, the media was changed. Test compounds were added (in triplicate) to the wells 24 hours after the media change, and four hours later 1 μCi $^3$H-Thymidine in 50 μl media was added per well. Cells were incubated for a further 24 hours. Media was removed from the cells, 10% ice cold trichloroacetic acid (TCA) added and plates were incubated on ice for 30 minutes. Cells were washed five times with 5% TCA and allowed to dissolve in 500 μl 10.1M NaOH for at least one hour (usually overnight). The preparations were neutralized with 0.1M HCl; 50 μl of the cell preparation was used to determine total protein content. Disintegrations per minute (DPM) from $^3$H labelling of DNA was determined by liquid scintillation counting of 900 μl of the cell preparation. Thymidine incorporation results were expressed as DPM/μg protein.

EXAMPLE 1

Retinoic Acid is More Effective Than Retinol at Increasing Keratinocyte Proliferation A. The effect on incorporation of $^3$H-thymidine μg soluble protein 24 hours after the addition of retinoic acid or retinol at various concentrations was examined. The results that were obtained are summarized in Table 1.

TABLE 1

Effect of Retinoic Acid (RA) and Retinol (ROH) on Keratinocyte Thymidine Incorporation

| Treatment | mean Thymidine incorp./µg protein ± s.d (% control) | p value vs Control | p value vs $10^{-7}$M ROH | p value vs $10^{-8}$M ROH | p value vs $10^{-9}$M ROH |
|---|---|---|---|---|---|
| Control | 2094 ± 140 (100%) | — | 0.202 | 0.501 | 0.203 |
| 2.5 × $10^{-7}$M RA | 2475 ± 116 (118%) | 0.005 | 0.032 | 0.004 | 0.002 |
| 2.5 × $10^{-7}$M ROH | 2218 ± 73 (106%) | 0.202 | — | 0.021 | 0.005 |
| 2.5 × $10^{-8}$M RA | 2686 ± 72 (128%) | 0.001 | 0.001 | 0.001 | 0.001 |
| 2.5 × $10^{-8}$M ROH | 2034 ± 46 (97%) | 0.501 | 0.021 | — | 0.121 |
| 2.5 × $10^{-9}$M RA | 2556 ± 80 (122%) | 0.001 | 0.006 | 0.001 | 0.001 |
| 2.5 × $10^{-9}$M ROH | 1977 ± 19 (94%) | 0.203 | 0.005 | 0.121 | — | n = 3

All concentrations of retinoic acid tested, i.e., 2.5×$10^{-7}$M, 2.5×$10^{-8}$ and 2.5×$10^{-9}$M, significantly increased keratinocyte proliferation over both the ethanol control and each of the 2.5×$10^{-7}$M, 2.5×$10^{-8}$M and 2.5×$10^{-9}$M retinol treatments and they did so in a dose dependant manner. This is consistent with retinoic acid having a greater stimulatory effect on epithelial proliferation than retinol.

EXAMPLE 2

Melinamide and Retinol Act Synergistically to Enhance Keratinocyte Proliferation The effect on incorporation of $^3$H-thymidine/µg soluble protein 24 hours after addition of the test compounds was examined and the combined results of three independent experiments were normalized to their respective ethanol controls. The results that were obtained are summarized in Table 2.

TABLE 2

Effect of Retinol and Melinamide on Keratinocyte Thymidine Incorporation

| Treatment | mean Thymidine incorp/µg protein ± s.d (% control) | p value vs Control | p value vs $10^{-8}$ ROH | p value vs $10^{-8}$ RA | p value vs $10^{-7}$ Mel |
|---|---|---|---|---|---|
| Control | 5176 ± 223 (100%) | — | — | — | — |
| 2.5 × $10^{-8}$M RA | 6711 ± 402 (130%) | 0.004 | 0.025 | — | — |
| 2.5 × $10^{-8}$M Retinol | 3956 ± 1303 (76%) | 0.185 | — | 0.025 | — |
| $10^{-7}$M Melinamide | 4695 ± 324 (91%) | 0.115 | — | — | — |
| 2.5 × $10^{-8}$M ROH + $10^{-7}$M Melinamide | 5776 ± 265 (112%) | 0.040 | 0.077 | 0.028 | 0.011 | n = 3

2.5×$10^{-8}$M retinoic acid significantly increased keratinocyte thymidine incorporation by 30% over both the ethanol control and the 2.5×$10^{-8}$M retinol treatment. $10^{-7}$M melinamide had no effect on keratinocyte proliferation on its own. However, the combination of 2.5×$10^{-8}$M retinol+$10^{-7}$M melinamide significantly increased keratinocyte proliferation over both the ethanol and the 2.5×$10^{-8}$M retinol treatments by 12% and 36% respectively. Melinamide and retinol therefore, act synergistically to increase keratinocyte proliferation mimicking the stimulatory effect of retinoic acid.

EXAMPLE 3

Melinamide and Retinyl Palmitate Synergistically Enhanced Keratinocyte Proliferation The effect of melinamide and the retinyl ester (retinyl palmitate) on incorporation of $^3$H-thymidine was examined. The results that were obtained are summarized in Table 3.

TABLE 3

Effect of Retinol and Melinamide on Keratinocyte Thymidine Incorporation

| Treatment | mean Thymidine incorp/µg protein ± s.d (% control) | p value vs Control | p value vs $10^{-7}$ RP | p value vs $10^{-7}$ RA | p value vs $10^{-7}$ Mel |
|---|---|---|---|---|---|
| Control | 5498 ± 484 (100%) | — | — | — | — |
| 2.5 × $10^{-7}$M RA | 7795 ± 370 (142%) | 0.003 | 0.001 | — | — |
| 2.5 × $10^{-7}$M Retinyl palmitate | 5746 ± 113 (104%) | 0.436 | — | 0.001 | — |
| $10^{-7}$M Melinamide | 4635 ± 608 (84%) | 0.127 | — | — | — |
| 2.5 × $10^{-7}$M ROH + $10^{-7}$M Melinamide | 6395 ± 286 (116%) | 0.050 | 0.022 | 0.007 | 0.010 |

2.5×$10^{-7}$M retinoic acid significantly increased keratinocyte thymidine incorporation over both the ethanol control and the 2.5×$10^{-7}$M retinyl palmitate treatment by 38%. $10^{-7}$M melinamide had no effect on keratinocyte proliferation on its own. However, the combination of 2.5×$10^{-7}$M retinyl palmitate+$10^{-7}$M melinamide significantly increased keratinocyte proliferation over both the ethanol (by 16%) and the 2.5×$10^{-7}$M retinyl palmitate control treatments (by 12%). Melinamide and retinol therefore, act synergistically to increase keratinocyte proliferation mimicking the stimulator/effect of retinoic acid.

Examples 1–3 demonstrate that retinoic acid, in a dose dependent manner, increased thymidine incorporation in skin keratinocytes. In other words retinoic acid increased keratinocyte proliferation. In Examples 1–3, retinoic acid was used as positive control and reference compound against which the other compounds under analysis were compared. Retinol was completely ineffective at increasing keratinocyte proliferation.

The unexpected results of Examples 1–3, however, were that the effect of retinol on cultured keratinocytes can be enhanced to levels approaching those of retinoic acid by combining retinol or retinyl ester with melinamide—a compound which exerts little or no benefit on its own. The results documented above demonstrate that melinamide acts synergistically with retinol or retinyl ester, to increase keratinocyte proliferation, mimicking the effect of retinoic acid.

EXAMPLE 4

This example illustrates a high internal phase water-in-oil emulsion incorporating the inventive composition.

|  | % w/w |
| --- | --- |
| Retinol | 0.5 |
| Fully hydrogenated coconut oil | 3.9 |
| Melinamide | 5 |
| Brij 92* | 5 |
| Bentone 38 | 0.5 |
| MgSO₄7H₂O | 0.3 |
| Butylated hydroxy toluene | 0.01 |
| Perfume | qs |
| Water | to 100 |

*Brij 92 is polyoxyethylene (2) oleyl ether

EXAMPLE 5

This example illustrates an oil-in-water cream incorporating the inventive composition.

|  | % w/w |
| --- | --- |
| Retinoic acid | 0.15 |
| Mineral oil | 4 |
| Melinamide | 1 |
| Brij 56* | 4 |
| Alfol 16RD* | 4 |
| Triethanolamine | 0.75 |
| Butane-1,3-diol | 3 |
| Xanthan gum | 0.3 |
| Perfume | qs |
| Butylated hydroxy toluene | 0.01 |
| Water | to 100 |

*Brij 56 is cetyl alcohol POE (10)
Alfol 16RD is cetyl alcohol

EXAMPLE 6

This example illustrates an alcoholic lotion incorporating the composition according to the invention.

|  | % w/w |
| --- | --- |
| Retinyl palmitate | 0.15 |
| Melinamide | 0.1 |
| Ethanol | 40 |
| Perfume | qs |
| Butylated hydroxy toluene | 0.01 |
| Water | to 100 |

EXAMPLE 7

This example illustrates another alcoholic lotion containing the inventive composition.

|  | % w/w |
| --- | --- |
| Retinol | 0.15 |
| Melinamide | 0.1 |
| Ethanol | 40 |

-continued

|  | % w/w |
| --- | --- |
| Antioxidant | 0.1 |
| Perfume | qs |
| Water | to 100 |

EXAMPLE 8

This example illustrates a suncare cream incorporating the composition of the invention:

|  | % w/w |
| --- | --- |
| Retinol | 0.01 |
| Melinamide | 0.1 |
| Silicone oil 200 cts | 7.5 |
| Glycerylmonostearate | 3 |
| Cetosteryl alcohol | 1.6 |
| Polyoxyethylene-(20)-cetyl alcohol | 1.4 |
| Xanthan gum | 0.5 |
| Parsol 1789 | 1.5 |
| Octyl methoxycinnate (PARSOL MCX) | 7 |
| Perfume | qs |
| Color | qs |
| Water | to 100 |

EXAMPLE 9

This example illustrates a non-aqueous skin care composition incorporating the inventive combination.

|  | % w/w |
| --- | --- |
| Retinoic acid | 0.15 |
| Melinamide | 1 |
| Silicone gum SE-30[1] | 10 |
| Silicone fluid 345[2] | 20 |
| Silicone fluid 344[3] | 55.79 |
| Squalene | 10 |
| Linoleic acid | 0.01 |
| Cholesterol | 0.03 |
| 2-hydroxy-n-octanoic acid | 0.7 |
| Vitamin E linoleate | 0.5 |
| Herbal oil | 0.5 |
| Ethanol | 2 |

[1] A dimethyl silicone polymer having a molecular weight of at least 50,000 and a viscosity of at least 10,000 centistokes at 25° C., available from GEC
[2] Dimethyl siloxane cyclic pentamer, available from Dow Corning Crop.
[3] Dimethyl siloxane tetramer, available from Dow Corning Corp.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A skin conditioning composition comprising (a) from about 0.001% to about 10% of a compound selected from the group consisting of retinoic acid, retinol and a retinyl ester;

(b) from about 0.0001% to about 50% of melinamide; and (c) a cosmetically acceptable vehicle.

2. The composition of claim 1 wherein the reinyl ester is selected from the group consisting of retinyl palmirate, retinyl acetate and retinyl propionate, and mixtures thereof.

3. The composition of claim 1 wherein ingredient (a) is retinol.

4. The composition of claim 1 wherein ingredient (a) is a retinyl ester.

5. A method of treating a skin condition selected from the group consisting of dry skin, photodamaged skin, wrinkles, age spots, aged skin, acne, skin lightening, psoriasis and atopic dermatosis, the method comprising applying to the skin the composition of claim 1.

* * * * *